United States Patent
Kikuchi et al.

(10) Patent No.: US 7,788,108 B2
(45) Date of Patent: Aug. 31, 2010

(54) CROSS-CONTAMINATION PREVENTION SYSTEM AND AUTOMATIC ANALYZER WHICH EQUIP FOR IT

(75) Inventors: Takahiro Kikuchi, Ohmiya (JP); Masami Hayashi, Naka (JP); Tomonori Mimura, Tomobe (JP); Mitsuo Hattori, Hitachinaka (JP); Takeshi Sato, Hitachinaka (JP)

(73) Assignees: Hitachi High-Technologies Corporation, Tokyo (JP); Hitachi Science Systems, Ltd., Ibaraki (JP)

( * ) Notice: Subject to any disclaimer, the term of this patent is extended or adjusted under 35 U.S.C. 154(b) by 971 days.

(21) Appl. No.: 10/716,474

(22) Filed: Nov. 20, 2003

(65) Prior Publication Data
US 2004/0102997 A1 May 27, 2004

(30) Foreign Application Priority Data
Nov. 21, 2002 (JP) .............................. 2002-337355

(51) Int. Cl.
*G06Q 10/00* (2006.01)
(52) U.S. Cl. ....................... 705/1.1; 73/864.21; 165/206
(58) Field of Classification Search .................. 705/1, 705/1.1; 435/4
See application file for complete search history.

(56) References Cited

U.S. PATENT DOCUMENTS

| | | | | |
|---|---|---|---|---|
| 4,971,913 A | * | 11/1990 | Manabe et al. | 436/55 |
| 2002/0076352 A1 | * | 6/2002 | Motegi et al. | 422/64 |
| 2003/0129578 A1 | * | 7/2003 | Mault | 435/4 |

FOREIGN PATENT DOCUMENTS

| | | |
|---|---|---|
| EP | 1215502 | 6/2002 |
| JP | 5-240867 | 9/1993 |
| JP | 05-240867 | 9/1993 |
| JP | 07-270428 | 10/1995 |
| JP | 7-270428 | 10/1995 |
| WO | 98/45679 | 10/1998 |
| WO | 01-67113 A1 | 9/2001 |

* cited by examiner

*Primary Examiner*—Janice A. Mooneyham
*Assistant Examiner*—Heidi Riviere
(74) *Attorney, Agent, or Firm*—Mattingly & Malur, P.C.

(57) ABSTRACT

A period required for a time-consuming cross-contamination test is cut down or omitted, and a burden imposed on the customer by the costs of samples, reagents, etc. used in the test are reduced. A data failure caused by cross-contamination can be efficiently prevented. A maintenance service office establishes a connection via a communication line between a computer installed in the maintenance service office for maintenance of automatic analyzers and a customer's automatic analyzer or a personal computer placed in a customer's facility. The maintenance service office receives information regarding cross-contamination from reagent manufacturers and other customers (such as clinical examination rooms or centers) and validates it. The validated information is transmitted from the maintenance service office to the customer's automatic analyzer or personal computer via the communication line.

21 Claims, 13 Drawing Sheets

FIG.5

| No. | BARCODE No. OF OFFENSIVE REAGENT | | | REAGENT BARCODE No. OF DEFENSIVE REAGENT | | | LEVEL OF INFLUENCE OF CROSS-CONTAMINATION | WASHING METHOD | | |
|---|---|---|---|---|---|---|---|---|---|---|
| | MANU-FACTURER No. | TEST No. | LOT No. | MANU-FACTURER No. | TEST No. | LOT No. | | CONTAMI-NATION PLACE | DETER-GENT TYPE | DETER-GENT VOLUME (μL) |
| 1 | 111 | 01 | 000001 | 354 | 02 | 000023 | HIGH | FIRST REAGENT PROBE AND STIRRING ROD | HI-ALKALI D | 200 |
| 2 | 521 | 03 | 000002 | 332 | 06 | 000012 | MIDDLE | SECOND REAGENT PROBE AND STIRRING ROD | HI-ALKALI D | 200 |
| 3 | 451 | 06 | 000005 | 874 | 55 | 000021 | LOW | REACTION CUVETTE | HI-ALKALI D | 100+100 |
| ... | ... | ... | ... | ... | ... | ... | ... | ... | ... | ... |

FIG.6

|  | | WASHING ABILITY OF ANALYZER | | |
|---|---|---|---|---|
|  | | OK | GOOD | EXCELLENT |
| LEVEL OF INFLUENCE OF CROSS -CONTAMI-NATION | LOW | ADDITIONAL WASHING | NO ADDITIONAL WASHING | NO ADDITIONAL WASHING |
|  | MIDDLE | ADDITIONAL WASHING | ADDITIONAL WASHING | NO ADDITIONAL WASHING |
|  | HIGH | ADDITIONAL WASHING | ADDITIONAL WASHING | ADDITIONAL WASHING |

FIG.8

PLEASE CHECK TO ☐ OF THE PAIR WHICH PRESENTS CROSS-CONTAMINATION

| | No. | OFFENSIVE TEST | | | DEFENSIVE TEST | | |
|---|---|---|---|---|---|---|---|
| | | TEST NAME | REAGENT MANUFACTURER | REAGENT TYPE | TEST NAME | REAGENT MANUFACTURER | REAGENT TYPE |
| ☐ | 1 | ALP | A | R1 | Mg | B | R1 |
| ☐ | 2 | TG | C | R1 | Lip | D | R1 |

54 — 57 — 58 — 59 — 60 — 61 — 62

55 — YES    56 — CLOSE

CROSS-CONTAMINATION PREVENTION SYSTEM AND AUTOMATIC ANALYZER WHICH EQUIP FOR IT

BACKGROUND OF THE INVENTION

1. Field of the Invention

The present invention relates to a cross-contamination prevention system used in an automatic analyzer for qualitatively or quantitatively analyzing samples of a living body, such as serum and urine. More particularly, the present invention relates to a cross-contamination prevention system capable of greatly cutting down a preparation time required for setup of the analyzer, such as installation of the analyzer and introduction of a new reagent, and also relates to an automatic analyzer equipped with the cross-contamination prevention system.

2. Description of the Related Art

In an automatic clinical analyzer, it is general to employ a probe or the like in common for aspirating a sample, a reagent, etc. and dispensing them into another container, and to wash the probe or the like for reuse after aspirating one kind of sample, reagent, etc. In those pipetting steps, components of one sample, components of one reagent, and components of one reaction product, which have not been completely washed out, may mix with components of another sample, components of another reagent, and components of another reaction product, thereby giving rise to a reaction not intended and imposing an adverse influence upon a measured value of an item to be analyzed. Such an influence is called cross-contamination. A data failure caused by the cross-contamination has been prevented in the past as follows. An operator of the automatic analyzer inquiries a reagent manufacturer and an analyzer manufacturer of not only information regarding combinations (pairs) of reagents which may affect measured values by the cross-contamination, but also information regarding methods to prevent the influence. The operator actually carries out a cross-contamination test for a period of about 2 to 4 days, and validates the pairs causing the cross-contamination based on the test. The operation for preventing the cross-contamination is then carried out in consideration of the test result. In the prevention operation, information to prepare a program is entered on an operating screen to change the sequence of analyzing steps so that the pair of reagents causing the cross-contamination will not be analyzed in succession, or to insert a washing step with a detergent between steps of analyzing those reagents if the sequence of analyzing steps cannot be changed.

On the other hand, assuming a simultaneous measurement of, e.g., 10 items to be carried out in the validation test for the cross-contamination, there are a number 10×9=90 of item combinations that may possibly cause the cross-contamination. In the case of carrying out the validation test for 90 combinations, if a two-stage test made up of, for example, (1) a screening test and (2) a validation test is performed as usual, a test period of several days is required. Further, when new analysis items are added later after the start of routine analysis, an addition of the items increases the number of combinations to be tested in accordance with the equation of (the number of added items (1)×the number of all existing items (10)×2=20) for an addition of one item because the test is made on the added item with respect to each of all the existing items. Thus, the quantity of work required for the validation test is very large. The more the number of added items, the larger is the quantity of the required work. Further, information regarding the cross-contamination between reagents produced by different reagent manufacturers is sometimes not checked by the reagent manufacturers and therefore not sufficient. In such not a few cases, the operator must carry out the validation test for those reagents by himself or herself.

JP,A 5-240867 and JP,A 7-270428 propose it to cope with the above-mentioned problems by reducing time and labor required for item selection work, etc. in connection with the cross-contamination test. Also, JP,A 10-010131 proposes a method for enabling the operator to find an opponent item of the cross-contamination with high efficiency after a data failure has occurred by the cross-contamination.

SUMMARY OF THE INVENTION

Heretofore, as described above, customers and reagent manufacturers have carried out the cross-contamination test for each of automatic analyzers at the expense of long time and much labor by using large amounts of samples and reagents because there are differences among individual automatic analyzer units or differences among individual devices in an automatic analyzer unit. At the time of installation of an analyzer or at the start of the use of a new reagent, therefore, a period of one week or longer is taken until an examination of patient's samples can actually be started. For the purpose of realizing higher efficiency in management of an examination room or center, more importance has recently been placed on cut-down of an analyzer setup period at the time of installation, a saving of consumable goods such as samples and reagents, and cut-down of an evaluation period required prior to routine work for earlier starting of it. On the other hand, with introduction of new measuring systems and development of new item reagents, the number of combinations of reagents to be validated for the cross-contamination has increased monotonously. For those reasons, how to reduce the quantity of work required for a customer to carry out analyzer evaluation has become a major problem to be overcome.

Accordingly, it is an object of the present invention to greatly reduce a burden imposed on a customer by a time-consuming cross-contamination test, and to efficiently prevent a data failure caused by cross-contamination, thereby ensuring reliability of measured values in an automatic analyzer.

To achieve the above object, the present invention is constructed as follows:

1. A cross-contamination prevention system including a supervisor collecting, recording and managing information regarding cross-contamination that affects measured values with mixing of a plurality of reagents; a plurality of information offerers offering the cross-contamination information to the supervisor; a plurality of information receivers receiving the cross-contamination information from the supervisor; a communication system for dispensing the cross-contamination information among the supervisor, the plurality of information offerers, and the plurality of information receivers via communication lines; and a processing system for periodically sending the cross-contamination information under management of the supervisor to the plurality of information receivers.

In the above description, the term "periodically" should be interpreted as having not such a strict meaning that "the cross-contamination information is sent exactly at the same time everyday", but such a broad meaning that "plural items of information are sent plural times", for example, once per day, once per month or once per year at the indefinite time. Also, the "supervisor", the "information offerer", and the "information receiver" are not limited to natural persons, and include persons, groups, companies, etc. The term "plurality of information receivers" primarily means that there are a plurality of different persons, groups, companies, etc. receiving the information, but does not exclude the case in which there are a plurality of information receivers in the same group or company, etc. The "communication lines" are not limited to particular ones, and may be wired or wireless, such as dedicated lines, telephone lines, or radio communications, so long as the information can be transmitted through them.

2. An automatic analyzer in which many kinds of samples and reagents are handled by repeatedly using common parts while washing the parts, the automatic analyzer comprising an information taking-in unit for automatically taking in information regarding cross-contamination via a communication line, the information including reagent combinations causing cross-contamination that affects measured values with mixing of a plurality of samples and reagents attributable to the use of the common parts; and the function of carrying out a cross-contamination prevention measure, including change in order of pipetting the reagents or insertion of a washing step with a detergent between steps of analyzing relevant reagents, to prevent the occurrence of the cross-contamination in accordance with the cross-contamination information taken in by the information taking-in unit.

BRIEF DESCRIPTION OF THE DRAWINGS

FIG. 5 is a table showing information regarding the cross-contamination in the automatic analyzer according to the first embodiment of the present invention;

FIG. 6 is a table showing the relationship between the washing ability and a level of influence of cross-contamination in the automatic analyzer according to the first embodiment of the present invention;

FIG. 8 shows an example of a prevention registration screen displayed when a pair of reagents causing the cross-contamination was found in the automatic analyzer according to the first embodiment of the present invention;

DESCRIPTION OF THE PREFERRED EMBODIMENTS

Figure 1:
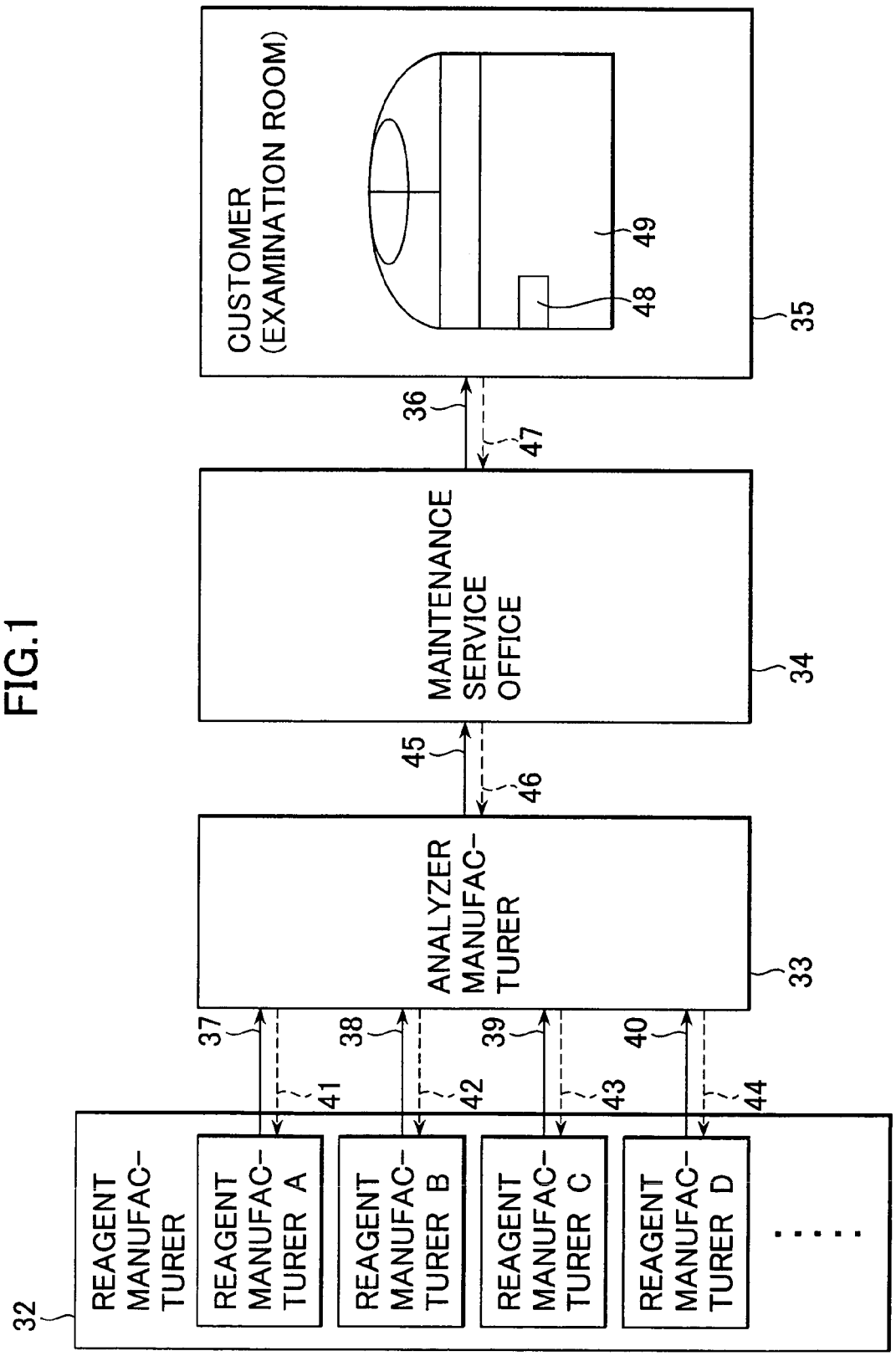
FIG. 1 is a block diagram showing a flow of cross-contamination information for an automatic analyzer according to a first embodiment of the present invention and charges paid in exchange for the cross-contamination information.

The present invention is primarily concerned with an automatic analyzer comprising a device for reading a reagent barcode affixed to a side surface of each reagent bottle to identify manufacture names and test items of regents set by an operator, and an input unit for inputting information regarding cross-contamination from the outside by using a public communication line, such as the Internet. The automatic analyzer receives the cross-contamination information from, for example, a computer installed for maintenance of automatic analyzers in a maintenance service office, with which a customer contracts a maintenance agreement, and stores the received information in a memory. If there is a reagent combination (pair) checked in the received information, the automatic analyzer is operated so as to prevent the corresponding cross-contamination in an automatic manner. Also, the present invention is concerned with a cross-contamination prevention system capable of dispensing the cross-contamination information as described above. However, the present invention can be implemented in many variations within the scope of the invention defined in the claims. Further, if kinds of reagents used and channel setting among the reagents are known, an analyzer manufacturer can carry out a cross-contamination test in response to a request from the customer before shipment of the analyzer, and then ship the analyzer after registering a cross-contamination prevention program in it. As an alternative, it is also possible to set up a homepage on the Internet, to collect cross-contamination information from many indefinite customers (homepage members), and to make the information, for which a validation test has been carried out by the analyzer manufacturer, open to the homepage members.

The cross-contamination prevention system can be constructed, by way of example, as follows. A maintenance computer storing the cross-contamination information is installed in the maintenance service office, and a personal computer connected to the Internet, etc. is placed in a customer's examination room or center. The personal computer placed in the customer side may be provided as an operating unit of the automatic analyzer. The maintenance service office transmits the cross-contamination information to the customer via the Internet, etc. Upon looking at the transmitted information, the customer inputs, on a cross-contamination prevention screen displayed in the automatic analyzer, necessary data of the cross-contamination information (e.g., barcode No. of an offensive reagent, barcode No. of a defensive reagent, a level of Influence of cross-contamination, a contamination place, a detergent type, and a detergent volume) via communications, direct manual entry, or a storage medium, such as a flexible magnetic disk, for prevention of the cross-contamination.

Furthermore, the automatic analyzer according to the present invention has a built-in communication unit capable of being connected to the communication line, such as the Internet, so that it is able to not only receive the cross-contamination information from the maintenance service office, but also to transmit the cross-contamination information, which is stored in the analyzer, to the maintenance service office for accumulation of the cross-contamination information. The maintenance service office transmits, to the customer, the latest cross-contamination information that has been rearranged under management of the analyzer manufacturer, while the customer receives the transmitted information and utilizes it for prevention of the cross-contamination.

Embodiments of the present invention will be described in detail below with reference to the attached drawings.

First Embodiment

Figure 4:
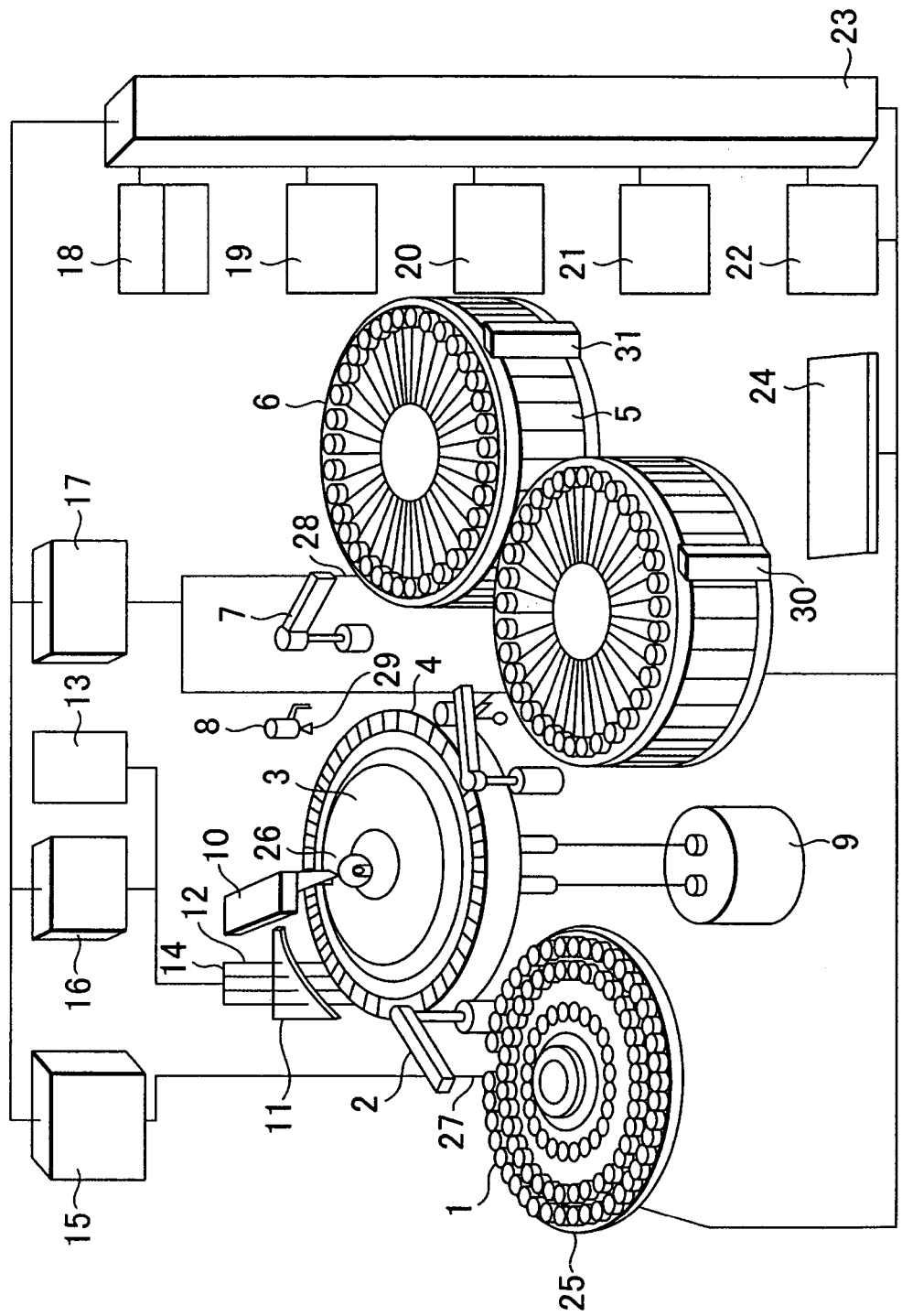
FIG. 4 is a schematic view for explaining the operation principle of the automatic analyzer according to the first embodiment of the present invention.

FIG. 4 is a schematic view for explaining the operation principle of the automatic analyzer according to the first embodiment of the present invention. The basic operation of the automatic analyzer will be described below. Reference numeral 1 denotes a sample disk on which a number of sample cups 25 are placed. A sample in each of the sample cups 25 is aspirated by a sample probe 27 of a sampling mechanism 2 and then injected into a predetermined reaction cuvette 4. Reference numeral 5 denotes a reagent disk on which a number of reagent bottles 6 are disposed. A reagent barcode reader 31 for the first reagent and a reagent barcode reader 30 for the second reagent are disposed aside two reagent disks in one-to-one relation. Further, a reagent pipetting mechanism 7 is disposed for each reagent disk 5. A reagent in each of the reagent bottles 6 is aspirated by a reagent probe 28 of the reagent pipetting mechanism 7 and then injected into a predetermined reaction cuvette 4.

Reference numeral 10 denotes a photometer, and numeral 26 denotes a light source lamp. Between the photometer 10 and the light source lamp 26, there is disposed a reaction disk 3 for containing samples to be measured. A large number, e.g., 120, of reaction cuvettes 4 are arranged on an outer periphery of the reaction disk 3. The reaction disk 3 is entirely held at a predetermined temperature by an incubator 9. Reference numeral 11 denotes a rinsing mechanism.

Also, the automatic analyzer comprises a microcomputer 19, an interface 23, a Log converter & A/D converter 18, a reagent pipetter 17, a pump 16 for washing water, and a sample pipetter 15. In addition, the automatic analyzer comprises a printer 20, a CRT 21, a hard disk 22 serving as a memory, and an operating unit 24.

In the automatic analyzer thus constructed, an operator inputs test selection data from the operating unit 24. The inputted test selection data is stored in a memory inside the microcomputer 19. A predetermined amount of a sample, which is put in the sample cup 25 and set in a predetermined position of the sample disk 1, is pipetted into the reaction cuvette 4 by using the sample pipetter 15 and the sample probe 27 of the sampling mechanism 2 in accordance with the test selection data stored in the memory inside the microcomputer 19. Thereafter, a sample probe 27 is washed by water. A predetermined amount of a reagent is then pipetted into the relevant reaction cuvette 4 by using the reagent probe 28 of the reagent pipetting mechanism 7. After washing the reagent probe 28 by water, it is employed again to pipette a reagent for the next reaction cuvette 4. A mixture of the sample and the reagent is stirred by a stirring rod 29 of a stirring mechanism 8. After washing the stirring rod 29 by water, it is employed again to stir a mixture in the next reaction cuvette 4. The reaction cuvette 4 is held at the predetermined temperature by the incubator 9 for development of a reaction. The progress of the reaction is measured by the photometer 10 at intervals of a constant time. The absorbance of the mixture is measured at two preset wavelengths. The measured absorbance is taken into the microcomputer 19 via the Log converter & A/D converter 18 and the interface 23.

The taken-in absorbance is converted to a concentration value, which is stored in the hard disk 22 and outputted to the printer 20. Additionally, the resulting examination data can also be displayed on the CRT 21.

The reaction cuvette 4 for which the measurement has completed is washed by the rinsing mechanism 11. The reaction cuvette having completed the washing is repeatedly employed for the next analysis.

FIG. 1 is a block diagram showing a flow of cross-contamination information for the automatic analyzer according to the first embodiment of the present invention and charges paid in exchange for the cross-contamination information is managed with participation of a reagent manufacturer 32, an analyzer manufacturer 33, a maintenance service office 34 as one example of an information supervisor, and a customer (examination room or examination center) 35. The reagent manufacturer 32 comprises, for example, a plurality of reagent manufacturers A, B, C and D. The cross-contamination information regarding reagents dealt by those reagent manufacturers is transmitted to the analyzer manufacturer 33 via information transmission media 37, 38, 39 and 40. The analyzer manufacturer 33 pays charges 41, 42, 43 and 44 in exchange for the transmitted information. The analyzer manufacturer 33 revalidates the cross-contamination information received from the plurality of the reagent manufacturers by making tests, puts results of the validation test together, and transmits the test results to the maintenance service office 34 via an information transmission medium 45. The maintenance service office 34 establishes a connection between a maintenance service computer in the office 35 via a communication (telephone) line 36, and sends the cross-contamination information to an input unit 48 of the automatic analyzer 49 via the communication line. The automatic analyzer 49 receives and stores the cross-contamination information. A maintenance agreement for prevention of the cross-contamination is contracted between the maintenance service office 34 and the customer 35, and a charge 47 in exchange for the maintenance service is paid from the customer 35 to the maintenance service office 34.

Figure 2:
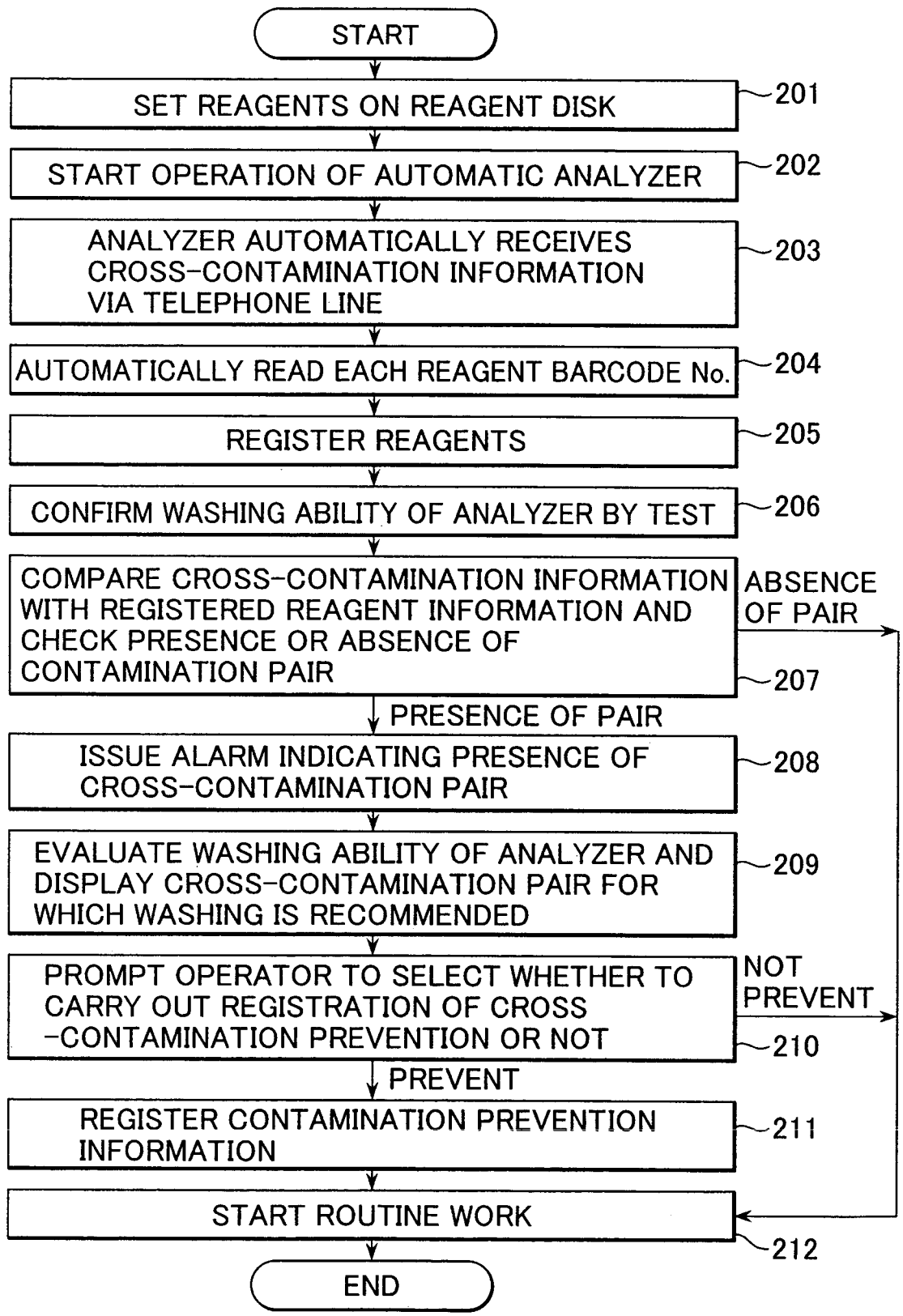
FIG. 2 is a flowchart showing the cross-contamination prevention function of the automatic analyzer according to the first embodiment of the present invention.

FIG. 2 is a flowchart showing a cross-contamination prevention method for use with the automatic analyzer according to this first embodiment. In step 201, the operator sets reagent bottles affixed with barcodes for reagent identification, which are used in a measurement, on the reagent disk of the automatic analyzer. When the operator turns on power supplied to the automatic analyzer in step 202, communication software incorporated in the boot-up processing is started up in step 203. The connection between the computer in the maintenance service office and the automatic analyzer is thereby established so that the analyzer automatically receives the cross-contamination information via the telephone line. By causing the automatic analyzer to receive the cross-contamination information every morning upon the startup, the cross-contamination information stored in the analyzer can always be updated to the latest information. The cross-contamination information received from the computer in the maintenance service office via communication is made up of, as shown in FIG. 5, "Barcode No. of Offensive Reagent (including Manufacturer No., Test No., and Lot No.), Barcode No. of Defensive Reagent (including Manufacturer No., Test No., and Lot No.), Level of Influence of Cross-contamination (high, middle and low), Contamination Place, Detergent Type, and Detergent Volume".

Figure 3:
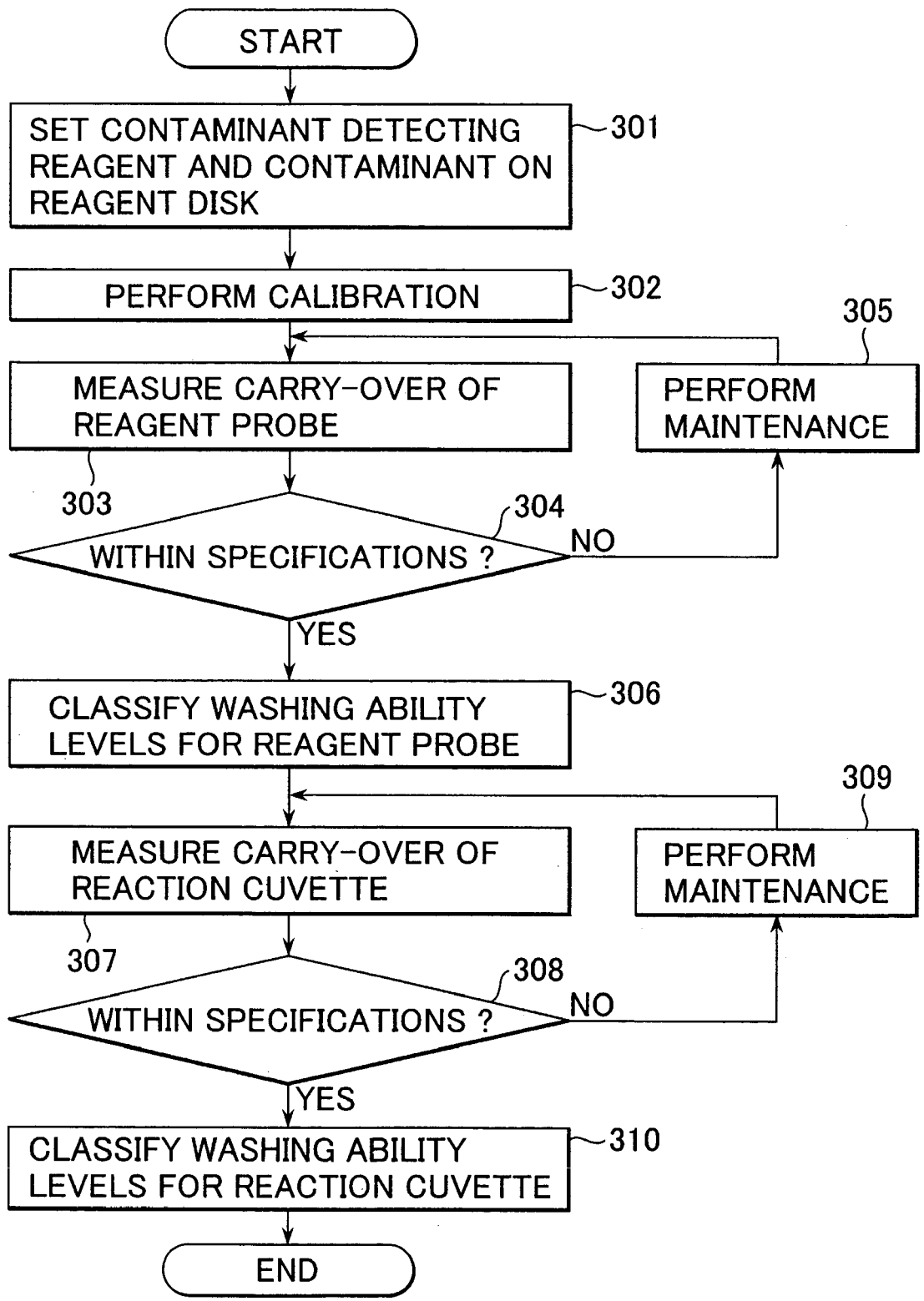
FIG. 3 is a flowchart showing a validation test for the washing ability of the automatic analyzer according to the first embodiment of the present invention.

The analyzer automatically reads, in step 204, a reagent barcode label affixed to a side surface of each reagent bottle for identification of the reagent, and then registers the reagents set on the reagent disk (step 205). When the washing ability of the analyzer has never been validated, or when the customer desires validation of the washing ability, a carry-over occurred upon transition from a phosphate buffer solution to an organic phosphate or the like is measured in step 206 with a one-touch operation for the purpose of validating the washing ability of the analyzer. FIG. 3 is a flowchart showing a method for validating the washing ability of the automatic analyzer. In step 301, the operator sets a contaminant detecting reagent and a contaminant on the reagent disk. In step 302, calibration of the contaminant detecting reagent is performed. In step 303, a carry-over of the reagent probe is measured. In step 304, it is determined whether the measured result of the carry-over of the reagent probe is within the specifications set by the analyzer manufacturer. If the measured result of the carry-over of the reagent probe is not within the specifications, the maintenance is performed in step 305 and the measurement is made again. In step 306, the washing ability for the reaction probe is classified into three levels, e.g., "excellent", "good" and "OK", which are used for determining whether the reagent probe is to be washed to cope with the cross-contamination. In step 307, a carry-over of the reaction cuvette is measured. In step 308, it is determined whether the measured result of the carry-over of the reaction cuvette is within the specifications set by the analyzer manufacturer. If the measured result of the carry-over of the reaction cuvette is not within the specifications, the maintenance is performed in step 309 and the measurement is made again. In step 310, the washing ability for reaction cuvette is classified into three levels, e.g., "excellent", "good" and "OK", which are used for determining whether the reaction cuvette is to be washed to cope with the cross-contamination.

Figure 7:
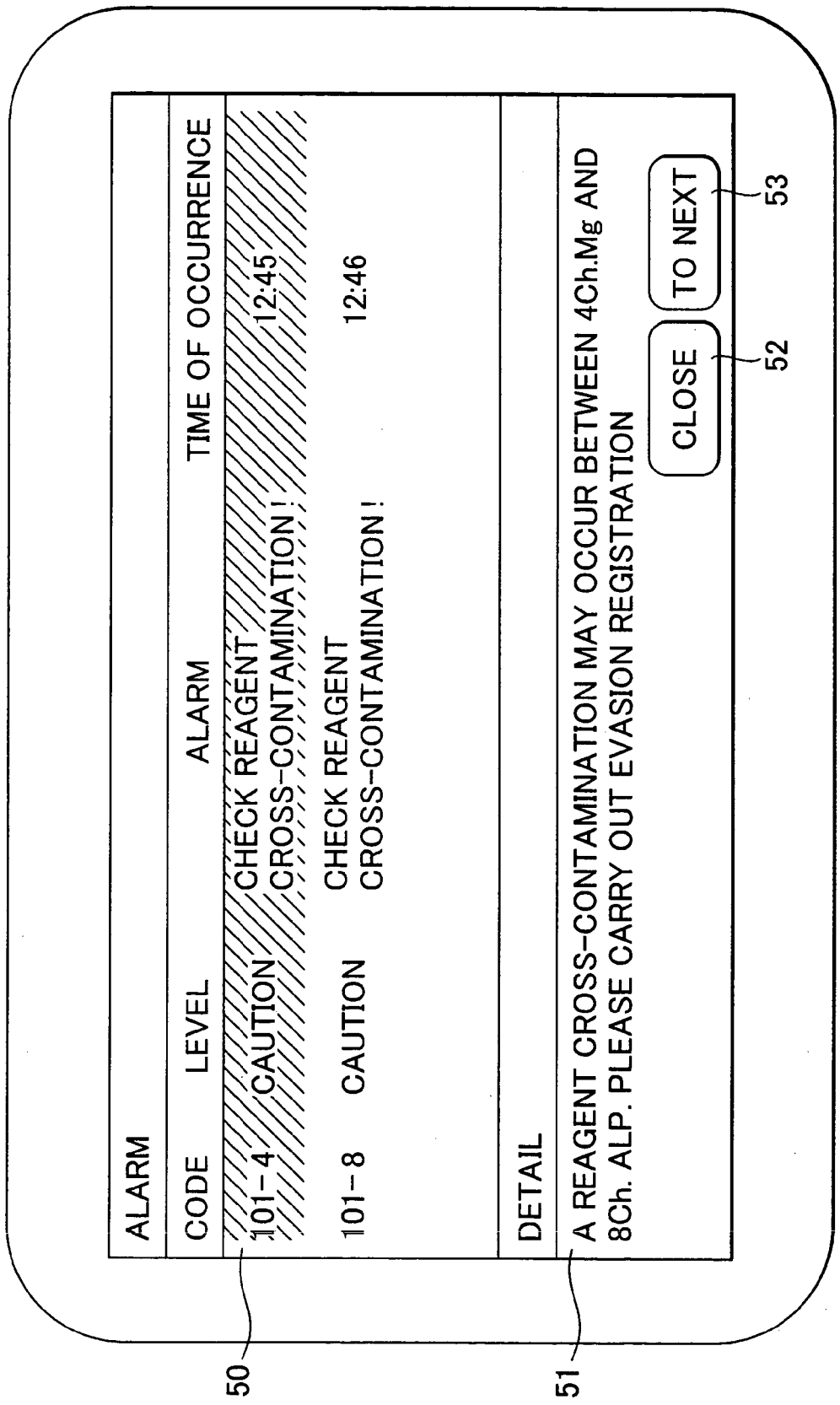
FIG. 7 shows an example of an alarm screen displayed when a pair of reagents causing the cross-contamination was found in the automatic analyzer according to the first embodiment of the present invention.

Returning to FIG. 2 again, in step 207, the reagent manufacturer name and the test information both contained in the reagent barcode are compared with the information of combinations (pairs) causing the cross-contamination, which is stored in the memory of the automatic analyzer, to check the presence or absence of a pair causing the cross-contamination. In the presence of a pair causing the cross-contamination, an alarm 50 including a message "Check reagent cross-contamination!" (see FIG. 7) is issued in step 208 to the pair for which the washing is recommended based on a determination logic in accordance with a table of FIG. 6, which shows the relationship between the actually measured washing ability of the analyzer and a level of influence of the cross-contamination. Then, when the operator depresses a "To Next" key 53 disposed in the lower right corner of FIG. 7, the analyzer displays a prevention registration screen. In steps 209 and 210 of FIG. 2, the operator selects for each cross-contamination pair whether registration of the cross-contamination prevention is to be carried out. The prevention registration screen, shown in FIG. 8, displays a prevention registration key 54, an offensive test name 57, an offensive reagent manufacture 58, an offensive reagent type 59, a defensive test name 60, a defensive reagent manufacture 61, and a defensive reagent type 62.

Figure 9:
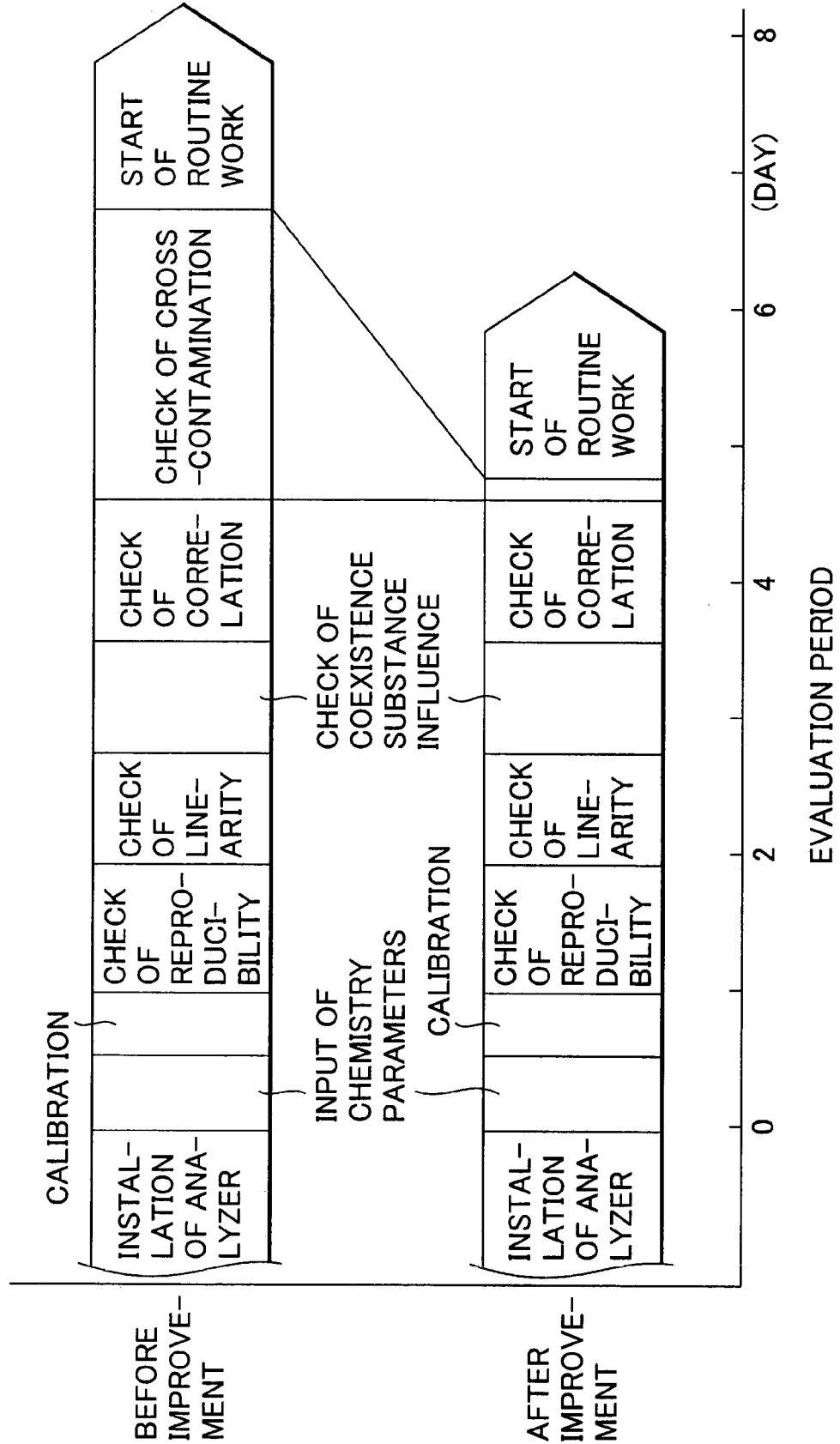
FIG. 9 is a chart showing, for comparison, installation periods of a known analyzer and the automatic analyzer according to the first embodiment of the present invention.

In step 211 of FIG. 2, for the cross-contamination pair which has been checked for registration to prevent the cross-contamination, the reagent manufacturer automatically prevention measures comprising, for example, washing by water, washing by a detergent, change in order of measuring steps, recommendation for setting of a detergent channel. Further, a serviceman can select upon switching-on/off whether the operator is allowed to look at the cross-contamination pair information without interfering business of each reagent manufacturer, by disclosing the cross-contamination information to the customer. In step 212, the operator starts routine work. According to this first embodiment, as seen from FIG. 9, it is possible to cut down the evaluation period about 2 days for medium and small size analyzers and about 4 days for large size analyzers in ordinary cases, and hence to advance the time of starting the routine work correspondingly.

Second Embodiment

Figure 10:
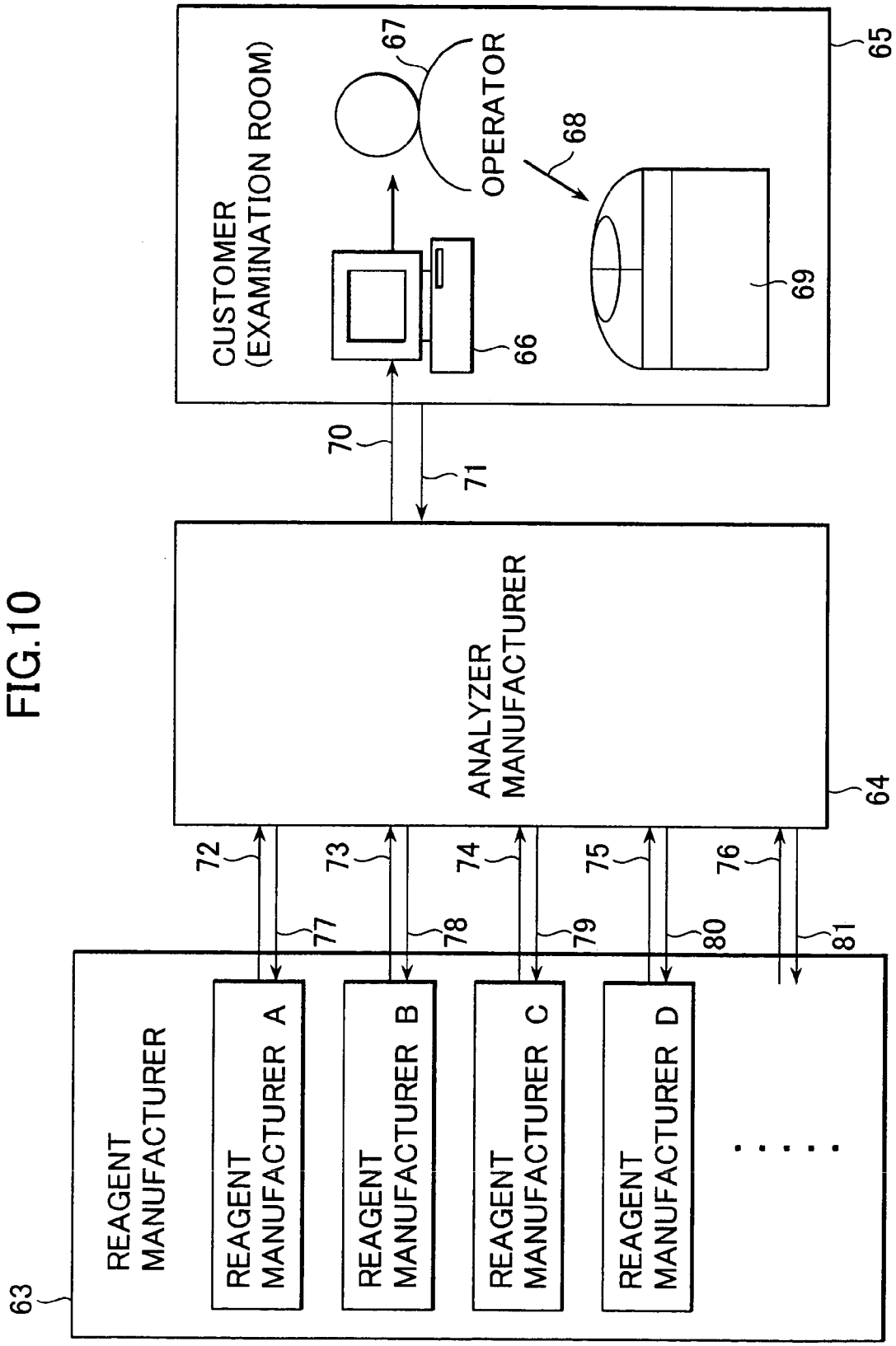
FIG. 10 is a block diagram showing a flow of cross-contamination information for an automatic analyzer according to a second embodiment of the present invention and charges paid in exchange for the cross-contamination information.

FIG. 10 is a block diagram showing a flow of cross-contamination information for an automatic analyzer according to a second embodiment of the present invention and charges paid in exchange for the cross-contamination information. In this second embodiment, cross-contamination information is managed with participation of a reagent manufacturer 63, an analyzer manufacturer 64 as one example of an information supervisor, and a customer (examination room or examination center) 65. The reagent manufacturer 63 comprises, for example, a plurality of reagent manufacturers A, B, C, D and so on. The cross-contamination information regarding reagents dealt by those reagent manufacturers is transmitted to the analyzer manufacturer 64 via information transmission media 72, 73, 74, 75 and 76. The analyzer manufacturer 64 pays charges 77, 78, 79, 80 and 81 to the reagent manufacturer 63 in exchange for the transmitted information. The analyzer manufacturer 64 makes a rearrangement and performs a validation test for the cross-contamination information received from the plurality of the reagent manufacturers. Then, the analyzer manufacturer 64 transmits the validated cross-contamination information to a customer's personal computer 66 placed in the examination room or center via a public transmission line such as the Internet. An operator 67 who operates an automatic analyzer 69 installed in the examination room or center is able to look at the cross-contamination information on a screen of the personal computer 66 and to download it into a memory of the personal computer. When a customer 65 accesses and obtains the cross-contamination information, the customer pays a charge via the Internet. Further, when the operator 67 looks at the cross-contamination information and finds a pair causing the cross-contamination among reagents used in the automatic analyzer 69, the operator manually directly inputs the washing conditions for prevention of the cross-contamination in accordance with the prevention information. As an alternative, the operator 67 inserts a flexible magnetic disk or the like, on which the cross-contamination information is recorded, into a flexible magnetic disk drive equipped in the analyzer operating unit, and then writes the washing conditions into the analyzer memory in response to instructions displayed on the screen. The automatic analyzer 69 carries out the operation for preventing the cross-contamination in accordance with the written cross-contamination information. The customer can update the written cross-contamination information as required.

The cross-contamination information received from the analyzer manufacturer 64 is made up of "Barcode No. of Offensive Reagent (including Manufacturer No., Test No., and Lot No.), Barcode No. of Defensive Reagent (including Manufacturer No., Test No., and Lot No.), Level of Influence of Cross-contamination (high, middle and low), Contamination Place, Detergent Type, and Detergent Volume".

Third Embodiment

Figure 11:
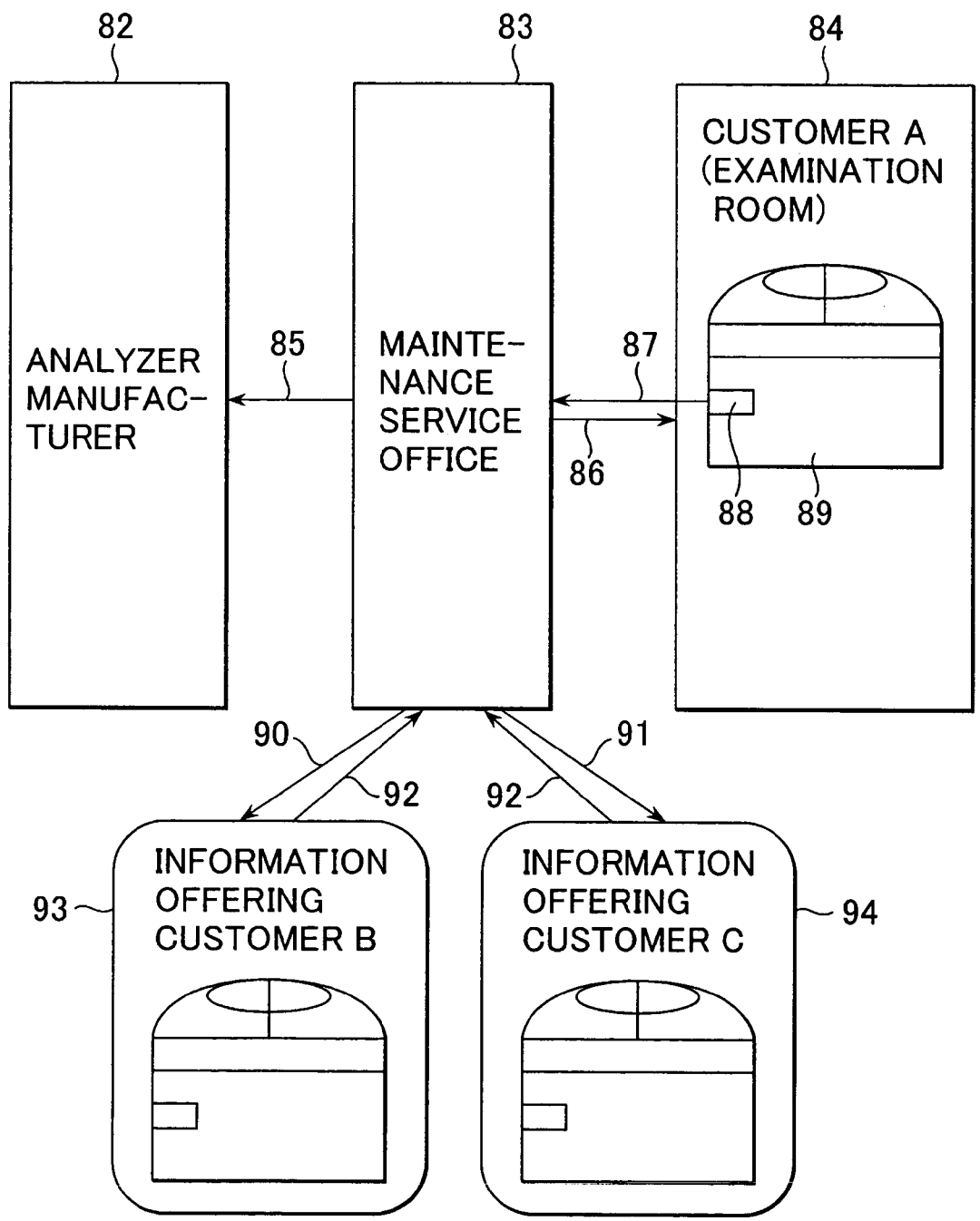
FIG. 11 is a block diagram showing a flow of cross-contamination information for an automatic analyzer according to a third embodiment of the present invention and charges paid in exchange for the cross-contamination information.

FIG. 11 is a block diagram showing a flow of cross-contamination information for an automatic analyzer according to a third embodiment of the present invention and charges paid in exchange for the cross-contamination information. In this third embodiment, cross-contamination information is managed with participation of an analyzer manufacturer 82, a maintenance service office 83, a customer (examination room or examination center) 84 purchasing the cross-contamination information, and customers (examination rooms or examination centers) 93, 94 offering the cross-contamination information. Individual data of cross-contamination information 92 obtained based on tests are stored in respective memories of automatic analyzers of the information offering customers 93, 94. The cross-contamination information 92 is transmitted from an input/output unit of each analyzer to the maintenance service office 83 via a communication line. The maintenance service office 83 pays charges 90, 91 in exchange for the transmitted cross-contamination information 92 to the customers 93, 94 having offered the cross-contamination information. The analyzer manufacturer manages the cross-contamination information received by the maintenance service office 83. The maintenance service office 83 sells cross-contamination information 86, which has been collected and validated under management of the analyzer manufacturer 82, to the customer 84 having signed a maintenance service office 83, and then receives a charge 87 in exchange for the cross-contamination information 86. The cross-contamination information is received by an input unit 88 and stored in an automatic analyzer 89 of the customer 84.

Fourth Embodiment

Figure 12:
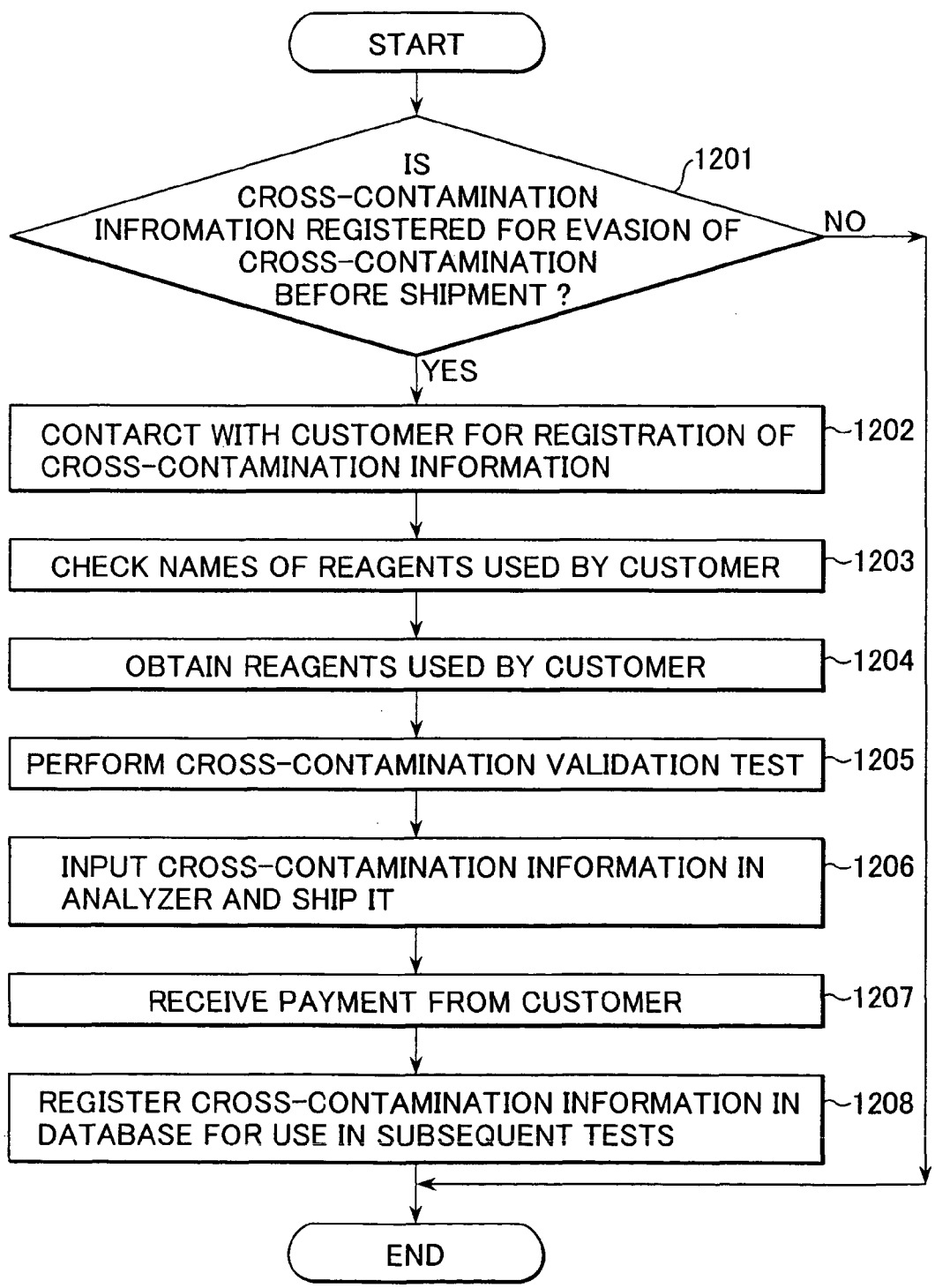
FIG. 12 is a flowchart of processing steps of a cross-contamination prevention system equipped in an automatic analyzer according to a fourth embodiment of the present invention.

In this fourth embodiment, cross-contamination information is managed with participation of a plurality of reagent manufacturers, an analyzer manufacturer, and a customer (such as a clinical examination room or center). For an automatic analyzer for which reagents to be used after update of the analyzer are already known for the reason of, e.g., continuous use of the same formula as before, the analyzer manufacturer carries out a cross-contamination test by using the reagents, which are to be used in the analyzer, in a factory of the analyzer manufacturer prior to shipment of the analyzer, inputs information to prevent the cross-contamination in accordance with the test results, and then ships the analyzer in a state capable of starting the routine work immediately after installation thereof. As an alternative, the analyzer manufacturer may deliver the automatic analyzer to the customer after carrying out the above-described operations in a customer's facility. The customer can save time and labor because of no need of carrying out the cross-contamination test, and hence can start the routine work at an earlier point in time. The analyzer manufacturer receives a charge from the customer in exchange for the serviced operations. FIG. 12 is a flowchart of processing steps executed in this fourth embodiment. In step 1201, a sales department of the analyzer manufacturer asks the customer for whether to register or not the information to prevent the cross-contamination. If the customer selects the registration, the registration of the cross-contamination evasion information is contracted in step 1202. In conformity with the contract, the analyzer manufacturer obtains, in step 1203, information regarding the names of reagents used by the customer and then, in step 1204, the reagents from the reagent manufacturers and the customer. A validation test for cross-contamination is carried out in step 1205. After inputting an evasion registration in accordance with results of the cross-contamination test, the analyzer manufacturer ships the automatic analyzer in step 1206. In the case of performing the cross-contamination test in the customer's facility, the automatic analyzer is delivered to the customer after the completion of the test. In step 1207, the analyzer manufacturer receives a charge in exchange for carrying out the cross-contamination test from the customer. In step 1208, the analyzer manufacturer stores the cross-contamination information, which has been obtained based on the test, in a database under management of the analyzer manufacturer to increase the efficiency of subsequent cross-contamination tests carried out for other customers with the use of the stored information.

Fifth Embodiment

Figure 13:
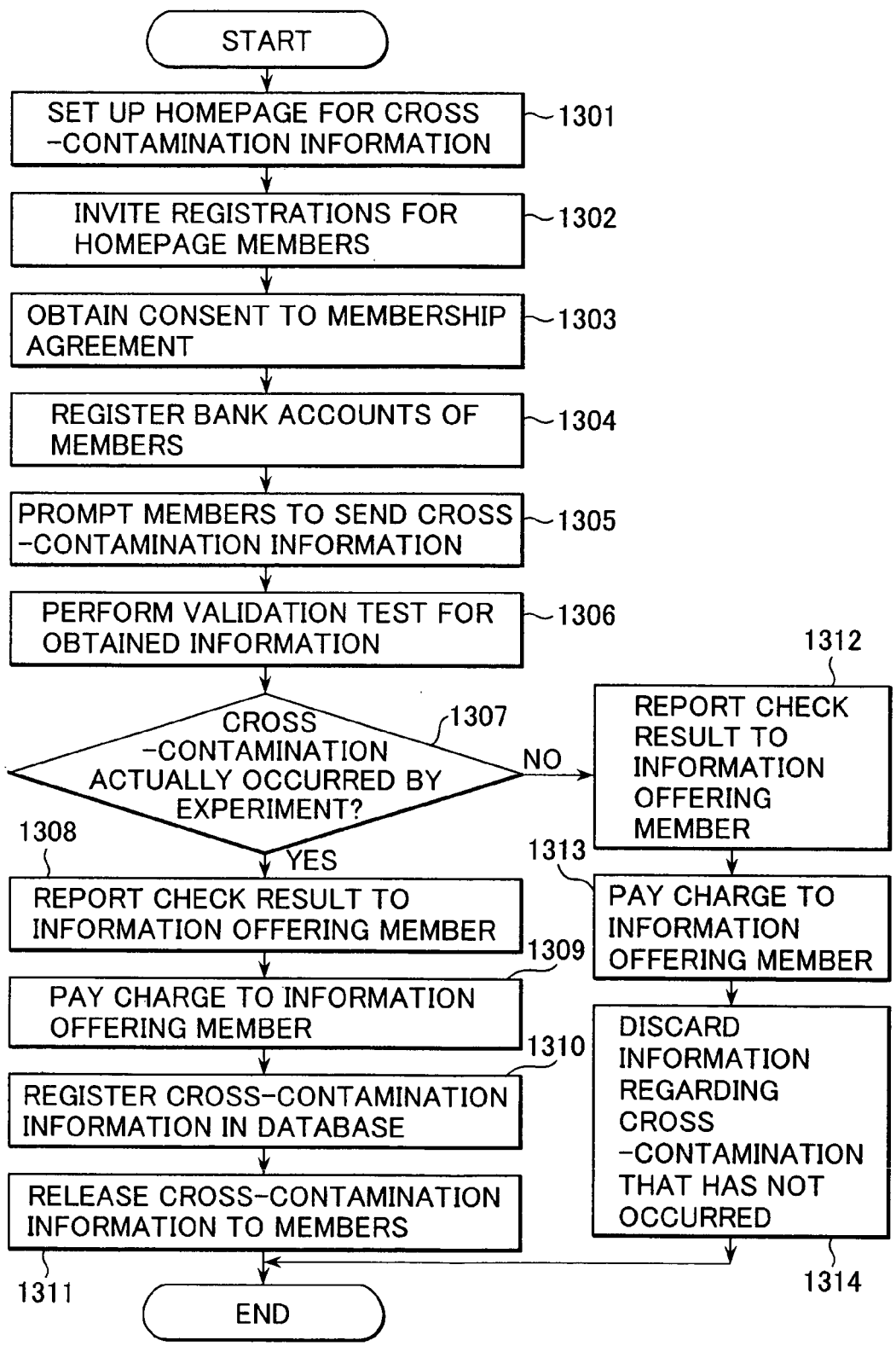
FIG. 13 is a flowchart of processing steps of a cross-contamination prevention system equipped in an automatic analyzer according to a fifth embodiment of the present invention.

FIG. 13 shows a fifth embodiment in which the cross-contamination information is collected and made open by utilizing a public communication line, such as the Internet. In step 1301, a homepage superintendent sets up a homepage in which the cross-contamination information is made open. The homepage superintendent invites registrations for homepage members in step 1302 and then, in step 1303, obtains member's consent to the membership agreement with understanding of the purpose of the homepage for offering the cross-contamination information. In step 1304, each member is prompted to register the bank account for payment of membership fees and charges in exchange for the offered information. In step 1305, the homepage superintendent calls for cross-contamination information from all of the members and receives the cross-contamination information via E-mail, etc. In step 1306, a validation test is made on the received information in a relevant factory. If it is determined in step 1307 that the cross-contamination has actually occurred, the measured result of the validation test is notified in step 1308 to the member who has offered the relevant information, and a charge, such as money or membership bonus points, is paid in step 1309 to the information offering member. In order to reduce possibility of receiving false information and to promote sending of true information, the charge is paid, for example, at different amounts set depending on whether the cross-contamination is false or true. If it is determined in step 1307 that the cross-contamination has not actually occurred, the measured result indicating no occurrence of the cross-contamination is notified in step 1312 to the member who has offered the relevant information, and a charge, such as money or membership bonus points, less than that paid in the case of receiving true information, is paid in step 1313 to the information offering member. In step 1314, the false cross-contamination information is discarded. In steps 1310 and 1311, the homepage superintendent registers in a database the cross-contamination information that has actually been validated by the test, and makes it open to the members.

The present invention can realize cut-down and omission of the evaluation period for the cross-contamination in the automatic analyzer. As seen from FIG. 9, the evaluation period for the cross-contamination in the automatic analyzer after installation has hitherto been about two or more days even for medium and small size analyzers and about one week or longer for large size analyzers. In contrast, according to the present invention, since the evaluation period after installation of the automatic analyzer can be omitted or cut down to several hours, a total evaluation period can be cut down eventually and hence a highly valuable effect can be achieved. Further, the cross-contamination information stored in the analyzer can always be updated to the latest information through communication upon every startup of the analyzer. Therefore, even when new test items are added upon change to new other reagents, it is possible to save time and labor required for the cross-contamination evaluation test to be made on the changed or newly added reagents.

What is claimed is:

1. A cross-contamination prevention system relating to an automatic analyzer having a reagent pipetting probe for pipetting a predetermined amount of a reagent into a reaction cuvette and a rinsing mechanism for rinsing said reagent pipetting probe, comprising:
   a maintenance office device for storing and receiving reagent cross-contamination information of a combination of an offensive reagent and a defensive reagent, with the defensive reagent to be affected by the offensive reagent;
   an information transmission unit connected to the maintenance office device and a first automatic analyzer via a first communication line, the information transmission unit transmitting reagent cross-contamination information obtained by a test using the first automatic analyzer; and
   an information receiver unit connected to the maintenance office device and a second automatic analyzer which is installed at the one or more customer's location, through a second communication line, the information receiver unit receiving the reagent cross-contamination information stored at the maintenance office device;
   wherein the maintenance office device includes a true or false validating unit to validate whether the reagent cross-contamination information transmitted from the information transmission unit is true or false; and
   wherein the maintenance office device includes a transmitting mechanism to transmit the reagent cross-contamination information stored in the maintenance office device and periodically judged to be true by the true or false validating unit to the information receiver unit; and
   wherein the maintenance office device transmits cross-contamination data to be managed by an analyzer manufacturer; and
   wherein the maintenance office charges fees in exchange for the cross-contamination information transmitted.

2. A cross-contamination prevention system according to claim 1, wherein the reagent cross-contamination information contains at least one of information for identifying an offensive reagent, information for identifying a defensive reagent, information regarding a level of influence of the cross-contamination, information regarding a contamination place, information regarding a detergent type, or information regarding a detergent volume.

3. A cross-contamination prevention system according to claim 1, wherein the second automatic analyzer connected to the information receiver unit includes an analyzer operating unit to change an operation sequence of the second automatic analyzer on the basis of the reagent cross-contamination information received by the information receiver unit.

4. A cross-contamination prevention system according to claim 3, wherein the second automatic analyzer connected to the information receiver unit includes a display unit to display the reagent cross-contamination information received by the information receiver unit, the display unit displaying an instruction to instruct the analyzer operating unit whether or not the operation sequence of the second automatic analyzer is to be changed.

5. A cross-contamination prevention system according to claim 4, wherein the second automatic analyzer connected to the information receiver unit includes a validation unit to validate an ability of suppressing cross-contamination of the second automatic analyzer, the display unit displaying the ability of suppressing cross-contamination of the second automatic analyzer.

6. A cross-contamination prevention system according to claim 1, wherein the maintenance office device determines a charge in exchange for reagent cross-contamination information transmitted from the information transmission unit based on whether the reagent cross-contamination information is judged to be true or false by the true or false validating unit.

7. A cross-contamination prevention system according to claim 1, wherein each of the first and second automatic analyzers is an automatic analyzer comprising:
   a memory to store reagent cross-contamination information; and
   an analyzer operating unit that receives instruction for changing an operation sequence of the automatic analyzer to prevent the occurrence of the cross-contamination on the basis of the reagent cross-contamination information stored in the memory, and carries out the operation sequence to prevent the occurrence of the cross-contamination in accordance with the received instruction.

8. A cross-contamination prevention system according to claim 1, wherein the second automatic analyzer connected to the information receiver unit is configured to automatically take in the cross-contamination information and change an operation sequence of the analyzer as required.

9. A cross-contamination prevention system according to claim 8, wherein the second automatic analyzer connected to the information receiver unit is configured to display the cross-contamination information having been automatically taken in, to ask an operator of the second automatic analyzer whether or not the operation sequence of the second automatic analyzer is to be changed, to register a result of confirmation made by the operator, and to change the operation sequence of the second automatic analyzer in accordance with the registration result.

10. A cross-contamination prevention system according to claim 9, wherein the second automatic analyzer connected to the information receiver unit is configured to validate its own ability of suppressing cross-contamination, and to determine whether or not the operation sequence of the second automatic analyzer is to be changed, based on a combination of the validated ability of suppressing cross-contamination and the cross-contamination information having been automatically taken in.

11. A cross-contamination prevention system according to claim 1, wherein each of the first and second automatic analyzers is an automatic analyzer which is configured to read a reagent barcode label of each of a plurality of reagent bottles for identification of reagents, to register the reagents, and to confirm washing ability of the automatic analyzer by testing.

12. A cross-contamination prevention system according to claim 11, wherein each of the first and second automatic analyzers is an automatic analyzer which is configured to:
   compare a reagent manufacturer name and test information contained in the reagent barcode label with information of combinations causing cross-contamination stored as reagent cross-contamination information in the memory to check for presence or absence of a combination causing cross-contamination;
   if there is presence of a combination causing cross-contamination, issue an alarm indicating the presence, evaluate the washing ability of the automatic analyzer and display the combination causing cross-contamination for which washing is recommended, and prompt an operator to select whether to carry out registration of cross-contamination prevention or not; and if the operator selects to carryout registration of cross-contamination prevention, register cross-contamination prevention information.

13. A cross-contamination prevention system relating to an automatic analyzer having a reagent pipetting probe for pipetting a predetermined amount of a reagent into a reaction cuvette and a rinsing mechanism for rinsing said reagent pipetting probe, comprising:

an maintenance office device storing reagent cross-contamination information of a combination of an offensive reagent and a defensive reagent to be affected by the offensive reagent;

an information transmission unit connected to the maintenance office device through a first communication line and a first automatic analyzer, the information transmission unit transmitting reagent cross-contamination information obtained by a test using the first automatic analyzer to the maintenance office device; and an information receiver unit connected to the maintenance office device through a second communication line and a second automatic analyzer, the information receiver unit receiving the reagent cross-contamination information stored in the maintenance office device from the maintenance office device;

wherein the maintenance office device includes a true or false validating unit to validate whether the reagent cross-contamination information transmitted from the information transmission unit is true or false;

wherein the maintenance office device includes a transmitting mechanism to transmit only the reagent cross-contamination information stored in the maintenance office device and judged to be true by the true or false validating unit to the information receiver unit;

wherein the maintenance office device transmits cross-contamination data to be managed by an analyzer manufacturer; and wherein the maintenance office charges fees in exchange for the cross-contamination information transmitted.

14. A cross-contamination prevention system according to claim 13, wherein the transmitting mechanism of the maintenance office device transmits only the reagent cross-contamination information that is judged to be true by the true or false validating unit to the information receiver unit periodically.

15. A cross-contamination prevention system according to claim 13, wherein the second automatic analyzer connected to the information receiver unit includes an analyzer operating unit to change an operation sequence of the second automatic analyzer on the basis of the reagent cross-contamination information received by the information receiver unit.

16. A cross-contamination prevention system according to claim 15, wherein the second automatic analyzer connected to the information receiver unit includes a display unit to display the reagent cross-contamination information received by the information receiver unit, the display unit displaying an instruction to instruct the analyzer operating unit whether or not the operation sequence of the second automatic analyzer is to be changed.

17. A cross-contamination prevention system according to claim 16, wherein the second automatic analyzer connected to the information receiver unit includes a validation unit to validate an ability of suppressing cross-contamination of the second automatic analyzer, the display unit displaying the ability of suppressing cross-contamination of the second automatic analyzer.

18. A cross-contamination prevention system according to claim 13, wherein the maintenance office device determines a charge in exchange for the reagent cross-contamination information transmitted from the information transmission unit based on whether the reagent cross-contamination information is judged to be true or false by the true or false validating unit.

19. A cross-contamination prevention system according to claim 13, wherein each of the first and second automatic analyzers is an automatic analyzer comprising:

a memory to store reagent cross-contamination information; and an analyzer operating unit that receives instruction for changing an operation sequence of the automatic analyzer to prevent the occurrence of the cross-contamination on the basis of the reagent cross-contamination information stored in the memory, and carries out the operation sequence to prevent the occurrence of the cross-contamination in accordance with the received instruction.

20. A cross-contamination prevention system according to claim 13, wherein each of the first and second automatic analyzers is an automatic analyzer which is configured to read a reagent barcode label of each of a plurality of reagent bottles for identification of reagents, to register the reagents, and to confirm washing ability of the automatic analyzer by testing.

21. A cross-contamination prevention system according to claim 20, wherein each of the first and second automatic analyzers is an automatic analyzer which is configured to:

compare a reagent manufacturer name and test information contained in the reagent barcode label with information of combinations causing cross-contamination stored as reagent cross-contamination information in the memory to check for presence or absence of a combination causing cross-contamination;

if there is presence of a combination causing cross-contamination, issue an alarm indicating the presence, evaluate the washing ability of the automatic analyzer and display the combination causing cross-contamination for which washing is recommended, and prompt an operator to select whether to carry out registration of cross-contamination prevention or not; and if the operator selects to carryout registration of cross-contamination prevention, register cross-contamination prevention information.

* * * * *